United States Patent
Suzuki et al.

(10) Patent No.: US 11,504,810 B2
(45) Date of Patent: Nov. 22, 2022

(54) CELL PROCESSING METHOD, LASER PROCESSING MACHINE

(71) Applicant: KATAOKA CORPORATION, Kyoto (JP)

(72) Inventors: Masami Suzuki, Kyoto (JP); Norio Nishi, Kyoto (JP); Junichi Matsumoto, Kyoto (JP)

(73) Assignee: KATAOKA CORPORATION, Kyoto (JP)

( * ) Notice: Subject to any disclaimer, the term of this patent is extended or adjusted under 35 U.S.C. 154(b) by 1153 days.

(21) Appl. No.: 15/739,395

(22) PCT Filed: Apr. 5, 2016

(86) PCT No.: PCT/JP2016/061078
§ 371 (c)(1),
(2) Date: Dec. 22, 2017

(87) PCT Pub. No.: WO2017/002422
PCT Pub. Date: Jan. 5, 2017

(65) Prior Publication Data
US 2018/0354076 A1    Dec. 13, 2018

(30) Foreign Application Priority Data
Jun. 29, 2015   (JP) .................. 2015-129636

(51) Int. Cl.
*C12Q 1/68* (2018.01)
*B23K 26/38* (2014.01)
(Continued)

(52) U.S. Cl.
CPC .......... *B23K 26/38* (2013.01); *B23K 26/0006* (2013.01); *B23K 26/12* (2013.01);
(Continued)

(58) Field of Classification Search
CPC ................... C12N 5/00; G01N 1/00
(Continued)

(56) References Cited

U.S. PATENT DOCUMENTS

2004/0084426 A1   5/2004   Okada
2010/0136690 A1   6/2010   Sundström et al.
(Continued)

FOREIGN PATENT DOCUMENTS

EP    1 849 861 A1    10/2007
JP    H 04/200380 A    7/1992
(Continued)

OTHER PUBLICATIONS

European Search Report dated Jan. 23, 2019 for European Patent Application No. 16817532.1-1132.
(Continued)

*Primary Examiner* — Aaron A Priest
(74) *Attorney, Agent, or Firm* — Scully, Scott, Murphy & Presser, P.C.

(57) ABSTRACT

In order to cut a plurality of clumps having an approximately uniform shapes and approximately uniform dimensions out of a cell aggregate which has proliferated and appropriately eliminate contamination with fragments of different shapes or dimensions, when cutting the clumps of approximately uniform shape out of the cell aggregate which has proliferated, cutting lines along which the clumps of a specific shape are cut out are set such that the area of a peripheral part of the cell aggregate which is not cut by the cutting line exceeds the surface area of one of the clumps, and the cell aggregate is cut by irradiating with laser light in such a way as to trace the cutting lines.

8 Claims, 4 Drawing Sheets

(51) Int. Cl.
*C12N 5/00* (2006.01)
*B23K 26/12* (2014.01)
*C12N 1/00* (2006.01)
*C12M 1/33* (2006.01)
*C12M 1/00* (2006.01)
*B23K 26/00* (2014.01)
*C12N 5/074* (2010.01)
*G01N 1/28* (2006.01)

(52) U.S. Cl.
CPC ............ *C12M 1/33* (2013.01); *C12M 45/02* (2013.01); *C12M 47/04* (2013.01); *C12N 1/00* (2013.01); *C12N 5/00* (2013.01); *C12N 5/0696* (2013.01); *G01N 2001/2886* (2013.01)

(58) Field of Classification Search
USPC ........................................................ 422/536
See application file for complete search history.

(56) References Cited

U.S. PATENT DOCUMENTS

2010/0184119 A1\* 7/2010 Bright .................... G01N 1/286
435/29

| | | | |
|---|---|---|---|
| 2013/0023025 A1 | 1/2013 | Sumaru et al. | |
| 2013/0045187 A1 | 2/2013 | Semechkin et al. | |
| 2015/0147301 A1 | 5/2015 | Semechkin et al. | |

FOREIGN PATENT DOCUMENTS

| | | |
|---|---|---|
| JP | 2010/081884 A | 4/2010 |
| JP | 2010/526530 A | 8/2010 |
| JP | 2012/514981 A | 7/2012 |
| JP | 2014/509192 A | 4/2014 |
| JP | 2015-054330 A | 3/2015 |
| WO | WO 2008/136729 A1 | 11/2008 |
| WO | WO 2010/081171 A2 | 7/2010 |
| WO | WO 2011/125615 A1 | 10/2011 |
| WO | WO 2012/112620 A1 | 8/2012 |

OTHER PUBLICATIONS

Japanese Office Action, dated Feb. 19, 2019, in Japanese Application No. 2015-129636 and English Translation thereof.
European Office Action, dated Dec. 2, 2019, in European Application No. 16 817 532.1-1132.
International Search Report (ISR) (PCT Form PCT/ISA/210), in PCT/JP2016/061078, dated Jul. 5, 2016.

\* cited by examiner

CELL PROCESSING METHOD, LASER PROCESSING MACHINE

TECHNICAL FIELD

The present invention relates to a method for cutting a plurality of clumps out of a cell aggregate which has proliferated and a laser processing machine used to perform the method.

BACKGROUND ART

Recently, fast growth has been witnessed in researches and developments of regenerative therapy technology and researches in drug discovery with the use of somatic stem cells, embryonic stem cells, induced pluripotent stem cells, and induced pluripotent stem cells. In these researches and developments, it is crucial to be able to produce desired cells and tissues in a large amount with high efficiency.

The process of cell culturing normally includes subculturing, which refers to the procedure of taking a cell clump out of a cell aggregate (colony) that has proliferated in a culture medium and then transferring the cell clump to a fresh culture medium for another round of proliferation (See following Patent Document, for example).

RELATED ART DOCUMENTS

Patent Documents

Patent document 1: Japanese Translation of PCT International Application Publication No. JP-T-2014-509192.

SUMMARY OF THE INVENTION

Problems to be Solved by the Invention

In order to prevent irregularity in conditions of growth of subcultured cells, it is desirable to substantially equalize the dimensions of each of a plurality of clumps in making the clumps by cutting a cell aggregate. However, when the cell aggregate is simply cut in such a way to draw grid-like cutting lines, parts near the outer edge of the cell aggregate become deformed and smaller in size than other parts that are cut into a square shape. In case of contaminating subcultured cells with those parts, there is concern about causing irregularity in conditions of growth of the cells after subculturing.

The present invention has paid attention to the above problem first, it is an object of the present invention to cut a plurality of clumps having approximately uniform dimensions out of a cell aggregate which has proliferated and appropriately eliminate contamination with fragments of different shapes or dimensions.

Means of Solving the Problems

A cell processing method according to the present invention for cutting a plurality of clumps having approximately uniform dimensions out of a cell aggregate which has proliferated is characterized by setting cutting lines along which the clumps of a specific shape are cut out such that the area of a peripheral part of the cell aggregate which is not cut by the cutting lines exceeds the area of one of the clumps.

A laser processing machine according to the present invention for cutting a plurality of clumps having approximately uniform dimensions out of a cell aggregate which has proliferated sets cutting lines along which the clumps of a specific shape are cut out such that the area of a peripheral part of the cell aggregate which is not surrounded by the cutting lines exceeds the area of one of the clumps, and cuts the cell aggregate by irradiating with laser light in such a way as to trace the cutting lines.

It is preferable that the cutting lines do not reach an outer edge of the cell aggregate.

Also, a laser processing machine according to the present invention for cutting a plurality of clumps having approximately uniform dimensions out of a cell aggregate which has proliferated cuts the cell aggregate by irradiating with laser light in such a way as to trace cutting lines along which the clumps of a specific shape are cut out, and irradiates a peripheral part of the cell aggregate with laser light in order to kill cells which exist in the peripheral part after irradiating with the laser light to trace the cutting lines or before irradiating with the laser light to trace the cutting lines.

Effects of the Invention

The present invention enables cutting a plurality of clumps having approximately uniform dimensions out of a cell aggregate which has proliferated and appropriately eliminating contamination with fragments of different shapes or dimensions.

MODE FOR CARRYING OUT THE INVENTION

Figure 1:
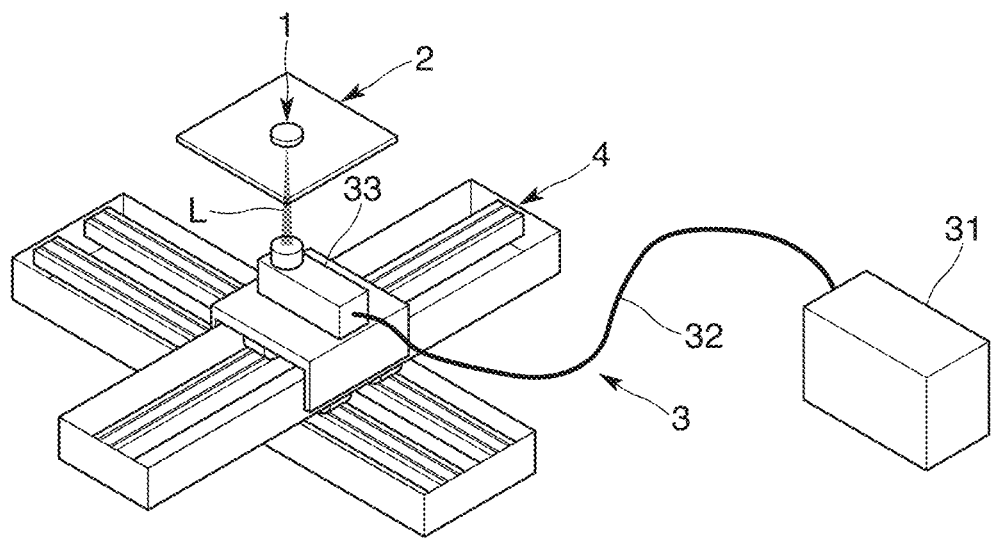
FIG. 1 is a schematic perspective view of a laser processing machine according to an embodiment of the present invention.

Described below is an embodiment of the present invention with reference to drawings. A laser processing machine according to this embodiment is configured to conduct laser processing to kill specific cells from among a group of cells cultured on a cell culture vessel 1. Japanese Patent Application No. 2015-111759 discloses the detail of the laser processing. Referring to FIG. 1, the laser processing machine principally consists of a support 2 supporting one or a plurality of cell culture vessels 1, a laser irradiator 3 configured to apply a laser beam L to the cell culture vessel 1 supported on the support 2, a displacement mechanism 4 configured to control the target location in the cell culture vessel 1 where the laser beam L is to be directed, and a control module 5 configured to control the laser irradiator 3 and the displacement mechanism 4.

It is preferable that the cell culture vessel 1 and the support 2 be disposed within a $CO_2$ incubator (not shown). The $CO_2$ incubator is a well-known device with its internal atmosphere being controllable in terms of $CO_2$ concentration and temperature. The $CO_2$ incubator is used in order to maintain a suitable cell-culturing environment, such as a suitable pH level of the culture medium in the cell culture vessel 1, during the laser processing.

The laser irradiator 3 comprises a laser source 31, a processing nozzle 33 configured to discharge the laser light L emitted from the laser source 31 toward the cell culture vessel 1, and an optical system 32 disposed between the laser source 31 and the processing nozzle 33 and configured to transfer the laser light L from the laser source 31 to the processing nozzle 33.

The laser source 31 is a device configured to oscillate a continuous-wave laser or pulsed laser L (the pulsed laser may be a high-frequency laser having a pulse width similar to that of a continuous wave). The laser L is not limited in terms of wavelength but may be a visible-light laser having such a wavelength as 405 nm, 450 nm, 520 nm, 532 nm, or 808 nm or an infrared laser, for example. It is necessary that energy of the laser L having the selected wavelength be absorbed by a to-be-irradiated layer 12 (described below) of the cell culture vessel 1. An ultraviolet laser having a wavelength of 380 nm or lower may undergo absorption by a DNA or a protein, potentially affecting cells. So, it is preferable that the wavelength of the laser L be greater than 380 nm. In this embodiment, the laser source 31 emits a continuous-wave diode laser having a wavelength near 405 nm and a maximum output of 5 W.

The processing nozzle 33 is equipped with, for example, a built-in lens that gathers the laser light L prior to irradiation of the to-be-irradiated layer 12 of the cell culture vessel 1 as well as a shutter or a mirror that switches between ON and OFF of the emission of the laser light L. The processing nozzle 33 is disposed below the cell culture vessel 1 supported on the support 2 and discharges the laser L upward. The optical axis of the laser beam L discharged from the processing nozzle 33 entries into the to-be-irradiated layer 12 of the cell culture vessel 1 at a substantially right angle.

The optical system 32 for transferring the laser L from the laser source 31 to the processing nozzle 33 may consist of any optical components such as an optical fiber, a mirror, and a lens.

The displacement mechanism 4 principally consists of an XY stage configured to displace the processing nozzle 33 of the laser irradiator 3 relative to the cell culture vessel 1 supported on the support 2. The XY stage 4 is a known XY stage capable of quickly moving an object disposed on a linear-motor sliding platform or the like in the X-axis direction (leftward and rightward) and in the Y-axis direction (frontward and backward) with precision. In this embodiment, the processing nozzle 33 is supported on the XY stage 4 and the processing nozzle 33 is moved relative to the support 2 and the cell culture vessel 1. An alternative configuration may also be adopted where the support 2 is supported on the XY stage 4 and both the support 2 and the cell culture vessel 1 are moved relative to the processing nozzle 33. In either case, the displacement mechanism 4 allows displacement of the target location on the to-be-irradiated layer 12 of the cell culture vessel 1 where the laser L is to be directed while maintaining a substantially constant angle between the to-be-irradiated layer 12 of the cell culture vessel 1 and the optical axis of the laser beam L.

Figure 2:
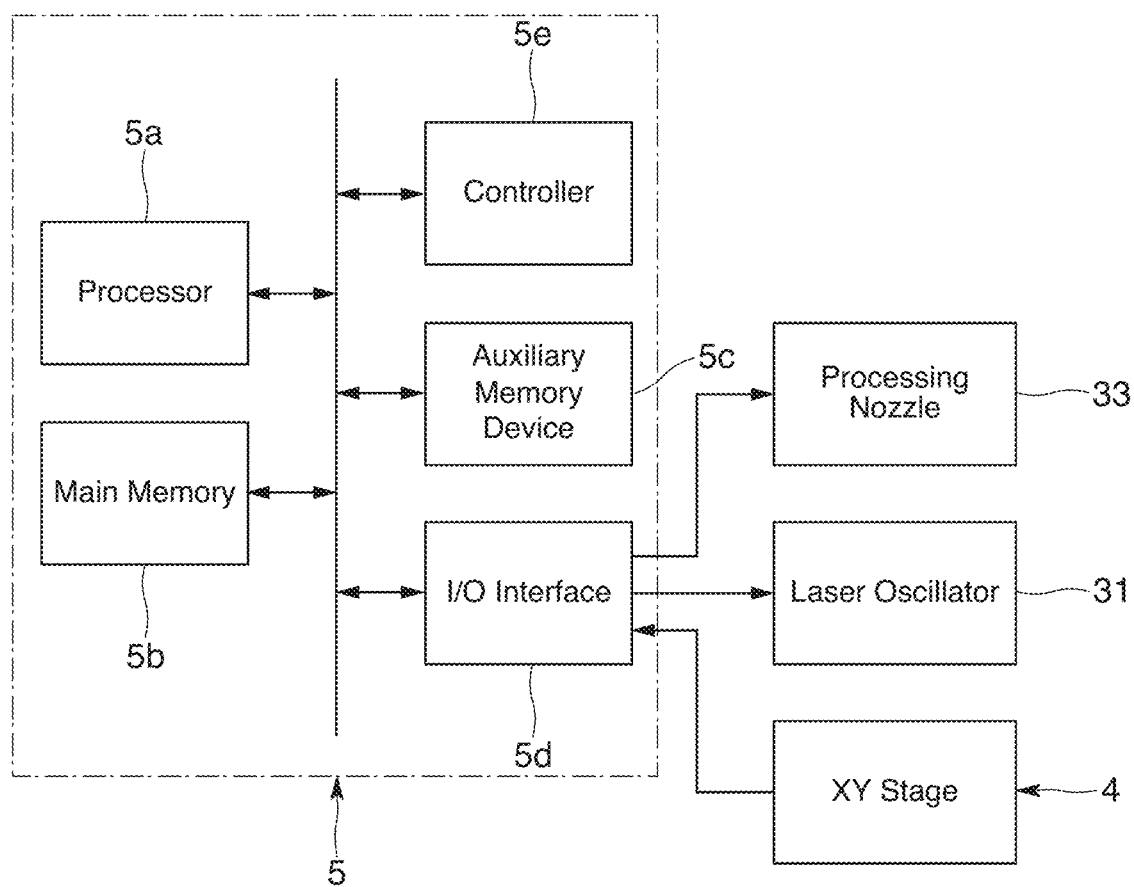
FIG. 2 is a diagram showing the configuration of hardware resources in the laser processing machine.

Referring to FIG. 2, the control module 5 consists of components such as a processor 5a, a main memory 5b, an auxiliary memory device 5c, a command-inputting device 5d, and an I/O interface 5e. Each of these components is controlled by a controller (such as a system controller or an I/O controller) to operate in coordination with the other components. The auxiliary memory device 5c is a flash memory or a hard drive, for example. The command-inputting device 5d is a device operable with a finger, such as a touch panel, a track pad, a pointing device like a mouse, a keyboard, or a push button. The I/O interface 5e may comprise a servo driver (servo controller). The control module 5 may consist of a general-purpose personal computer, a server computer, and a workstation, for example.

Figure 3:
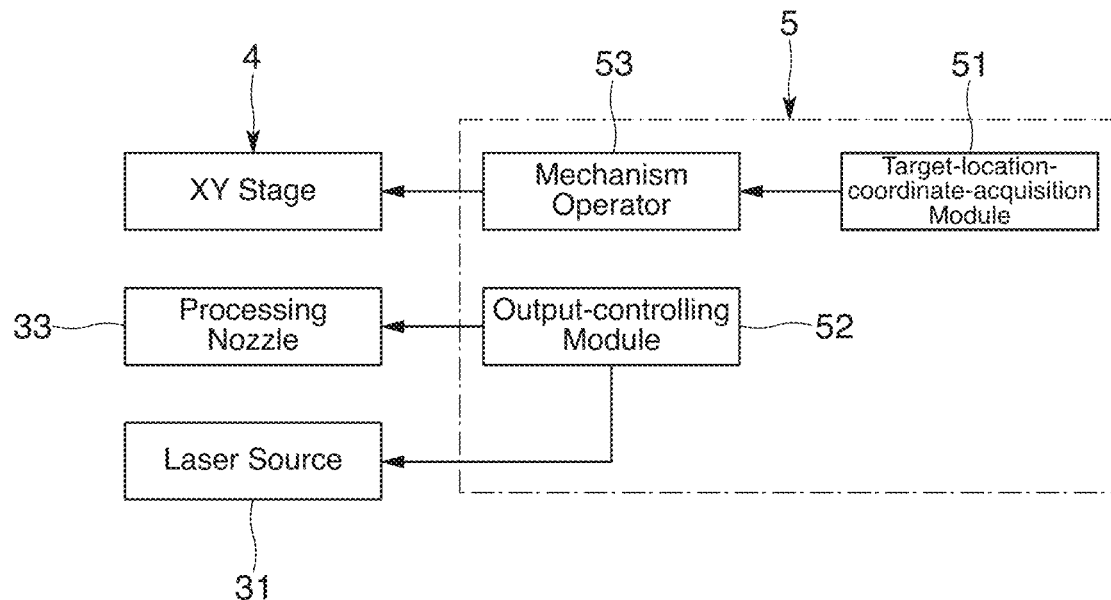
FIG. 3 is a functional block diagram of the laser processing machine.

The program to be run by the control module 5 is stored in the auxiliary memory device 5c. To run the program, the main memory 5b reads it and then the processor 5a interprets it. According to the program, the control module 5 functions as a target-location-coordinate-acquisition module 51, an output-controlling module 52, and a mechanism operator 53, as shown in FIG. 3.

The target-location-coordinate-acquisition module 51 is configured to acquire one or multiple sets of X-Y coordinates of the target location in the cell culture vessel 1 where the laser light L is to be directed. The X-Y coordinates herein are a set of coordinates of the position of the specific cells to kill from among the group of cells cultured in the cell culture vessel 1. The specific cells to kill refer to the following, for example: unwanted cells present together with cells or tissues to be cultured; or cells on cutting lines 62 by which a cell aggregate 6 in the cell culture vessel 1 is divided into a plurality of cell clumps 61 for subculturing, in other words, cells on the boundary between the cell clumps 61. The information on the coordinates of the target location where the laser light L is to be directed may be stored in advance in the main memory 5b or the auxiliary memory device 5c, or the coordinates of the target location may be manually specified by a user. The target-location-coordinate-acquisition module 51 acquires the information on the coordinates of the target location by reading it from the main memory 5b or the auxiliary memory device 5c or by receiving a command specifying the coordinates of the target location from a user via the command-inputting device 5d.

The coordinates of the target location where the laser light L is to be directed may also be acquired as follows: an image of the cell aggregate 6 in the cell culture vessel 1 is taken with a camera sensor such as a CCD or a CMOS; the resulting image is analyzed; and then the position of the unwanted cells or any other cells to kill is specified. To set the cutting lines 62 along which the clumps 61 are cut out of the cell aggregate 6 (or the X-Y coordinates on the cutting lines 62), it is preferable to detect an outer edge 64 of the cell aggregate 6 from the obtained image of the cell aggregate 6 in the cell culture vessel 1 and calculate lengths of the cutting lines 62 such that at least one end of each of the cutting lines 62 does not reach the outer edge 64 of the cell aggregate 6. Detection of the position of the cells to kill (more specifically, determination of the coordinates of the target location where the laser light L is to be directed (in particular, the cutting lines 62)) through image analysis may be conducted by the control module 5 itself or by an external device or computer (not shown) communicatively coupled to the control module 5. In the former case, the target-location-coordinate-acquisition module 51 acquires via the I/O interface 5e an image taken with the camera sensor and then analyzes the image to acquire the coordinates of the target location. In the latter case, the target-location-coordinate-acquisition module 51 receives the information on the coordinates of the target location from the external device or computer via the I/O interface 5e, thereby acquiring the coordinates of the target location.

The output-controlling module 52 is configured to control the ON-OFF state of the discharge of the laser L from the processing nozzle 33 toward the to-be-irradiated layer 12 of the cell culture vessel 1 and to control the output intensity of the laser L irradiating the to-be-irradiated layer 12, namely the amount of energy of the laser L. More specifically, the output-controlling module provides the processing nozzle 33 via the I/O interface 5e with a command signal for switching between ON and OFF of the discharge of the laser L from the processing nozzle 33 and also provides the processing nozzle 33 or the laser source 31 via the I/O interface 5e with a control signal for controlling the output of the laser L.

The mechanism operator 53 is configured to operate the XY stage 4 supporting the processing nozzle 33 so as to move the processing nozzle 33 toward the coordinates of the target location acquired by the target-location-coordinate-acquisition module 51, thereby directing the optical axis of the laser beam L discharged from the processing nozzle 33 to the coordinates of the target location. More specifically, the mechanism operator provides the XY stage 4 via the I/O interface 5e with a command signal related to the coordinates of the target location acquired by the target-location-coordinate-acquisition module 51. By discharging the continuous-wave laser L or the high-frequency pulsed laser L, which is almost like a continuous-wave laser, from the processing nozzle 33 while moving the processing nozzle 33 and thereby moving the laser beam L according to the coordinates of the target location that are changing with time, the target location where the laser L is to be directed can be continuously moved while the to-be-irradiated layer 12 of the cell culture vessel 1 is being irradiated.

An alternative procedure may also be adopted, which is conducted as follows: the processing nozzle 33 is moved relative to the cell culture vessel 1 in a fashion similar to raster scanning with the optical axis of the processing nozzle 33 moving across a certain region on (the to-be-irradiated layer 12 of) the cell culture vessel 1; and then when the optical axis of the processing nozzle 33 has reached directly below the specific cells to kill, the processing nozzle 33 discharges the laser L.

Figure 4:
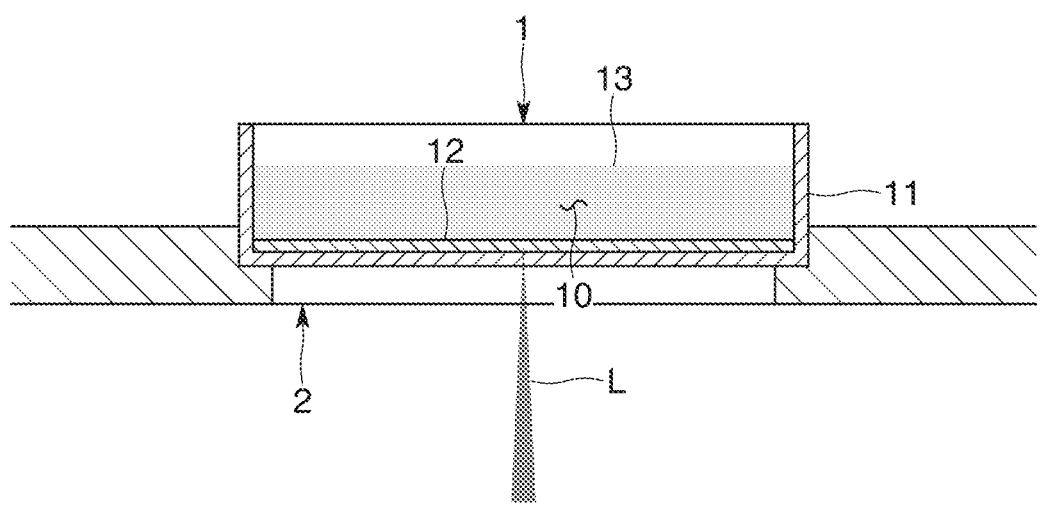
FIG. 4 is a sectional side view describing a cell processing method according to the embodiment.

Referring to FIG. 4, the cell culture vessel 1 according to this embodiment comprises a main body 11 passable by the laser light L discharged from the processing nozzle 33 and the to-be-irradiated layer 12 attached to the main body. The to-be-irradiated layer contains a photoresponsive ingredient capable of generating heat and/or acid upon irradiation with the laser light L.

The main body 11 is made of a material, such as plastic or glass, that is transparent or light-transmissive to allow the passage of a light having a wavelength within the range of wavelength of the laser L discharged from the processing nozzle 33. Examples of the plastic include polystyrene polymers, acrylic polymers (such as poly(methyl methacrylate) (PMMA)), polyvinylpyridine polymers (such as poly(4-vinylpyridine) and 4-vinylpyridine-styrene copolymer), silicone polymers (such as polydimethylsiloxane), polyolefin polymers (such as polyethylene, polypropylene, and polymethylpentene), polyester polymers (such as poly(ethylene terephthalate) (PET) and poly(ethylene naphthalate) (PEN)), polycarbonate polymers, and epoxy polymers. The main body 11 may be a commercially-available culture vessel, which may be used as it is. In terms of shape, the main body 11 may be a dish (petri dish), a multidish, or a flask, for example, just like the shape of a commercially-available culture vessel.

The light transmittance through the main body 11 which is made of polystyrene resin is very high, as high as 85% or higher at a light wavelength of about 380 nm or greater. As the light wavelength decreases from a light wavelength of about 380 nm, the light transmittance decreases (in other words, the light absorbance by the main body 11 increases). This phenomenon is probably caused by impurities contained in the polystyrene material.

It is preferable that the to-be-irradiated layer 12 be made of a polymer (polymeric material) that contains a pigment structure (chromophore) capable of absorbing a light having a wavelength within the range of wavelength of the laser L discharged from the processing nozzle 33. This is because such a polymer can be easily applied to the main body 11 for coating, can ensure necessary adhesion of the cells, and tends not to enter into the cells. Examples of the pigment structure capable of absorbing the laser light L include derivatives of organic compounds such as azobenzene, diarylethene, spiropyrane, spirooxazines, fulgides, leucopigments, indigo, carotinoids (such as carotene), flavonoids (such as anthocyanin), and quinoids (such as anthraquinone). Examples of the polymer backbone include acrylic polymers, polystyrene polymers, polyolefin polymers, polyvinyl acetate, polyvinyl chloride, polyolefin polymers, polycarbonate polymers, and epoxy polymers.

Below is a specific example of the pigment-structure-containing polymer in the to-be-irradiated layer 12, poly[methylmethacrylate-co-(Disperse Yellow 7 methacrylate)] (Chemical Formula 1, $(C_5H_8O_2)_m(C_{23}H_{20}N_4O_2)_n$). The azobenzene in this azo polymer may be unsubstituted azobenzene or one of various modified azobenzenes modified with a nitro group, an amino group, and/or a methyl group.

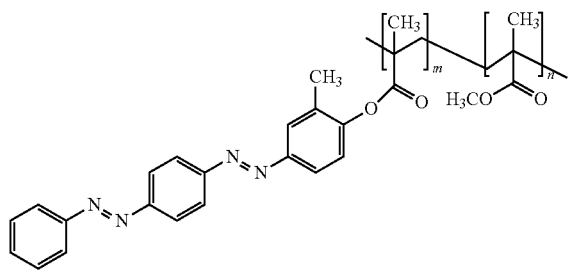

(Chemical Formula 1)

By applying a raw material liquid containing the pigment-structure-containing polymer described above or a raw material liquid containing the pigment-structure-containing polymer dissolved in a solvent (such as 1,2-dichloroethane or methanol) to the upward-facing surface of the main body 11, namely the bottom of a well 10, by spin coating, casting, or other techniques and then curing the raw material liquid, the to-be-irradiated layer 12 capable of generating heat upon irradiation with the laser light L can be formed. For example, by applying a polymer containing azobenzene as the pigment structure to the upward-facing surface of the main body 11, namely the bottom of the well 10, at a density of 7 µg/cm$^2$, the to-be-irradiated layer 12 having an average thickness of 70 nm can be formed on the bottom of the well 10. Alternatively, the main body 11 may be formed by using a material blend containing a pigment capable of absorbing the laser light L or by using the pigment-structure-containing polymer, and the resulting main body 11 has the function of the to-be-irradiated layer 12 capable of generating heat upon irradiation with the laser light L.

The light absorbance by the to-be-irradiated layer 12 which has a certain thickness and is made by coating the main body 11 with a polymer containing azobenzene as the pigment structure reaches its peak at a light wavelength of about 360 nm and then decreases as the light wavelength increases from about 360 nm. Although the light absorbance by the to-be-irradiated layer 12 at a light wavelength of about 425 nm or greater is lower than 20%, there remains a certain level of light absorbance at great light wavelengths. This phenomenon indicates that the to-be-irradiated layer 12 is well capable of absorbing the laser light L having a wavelength of 405 nm, 450 nm, 520 nm, or 532 nm.

In addition to or instead of the pigment-structure-containing polymer described above, the to-be-irradiated layer 12 may comprise a photoacid generator capable of generating an acidic substance upon irradiation with the laser light L. As disclosed in Patent Literature 1, it is preferable that a photoacid generator contain a pigment structure (chromophore) capable of absorbing a light having a wavelength within the range of wavelength of the laser L discharged from the processing nozzle 33 and also contain an acid precursor to be broken down into an acidic substance. Examples of the photoacid generator include sulfonic acid derivatives, carboxylic acid esters, onium salts, and photoacid-generating groups having a nitrobenzaldehyde structure.

Specific examples of the sulfonic acid derivatives as the photoacid generator include thioxanthone-based sulfonic acid derivatives (such as 1,3,6-trioxo-3,6-dihydro-1H-11-thia-azacyclopenta[a]anthracen-2-yl sulfonate) and naphthaleneimide-based sulfonic acid derivatives (such as 1,8-naphthalimide sulfonate). In addition to these, sulfonic acid derivatives such as disulfones, disulfonyldiazomethanes, disulfonylmethanes, sulfonylbenzoylmethanes, imidesulfonates, and benzoinsulfonates may also be used.

Examples of the carboxylic acid esters include 1,8-naphthalenedicarboxylic imide methylsulfonate and 1,8-naphthalenedicarboxylic imide tosyl sulfonate. Examples of the onium salts include sulfonium salts and iodonium salts containing an anion, such as tetrafluoroborate ($BF_4^-$), hexafluorophosphate ($PF_6^-$), and hexafluoroantimonate ($SbF_6^-$).

By applying a raw material liquid containing a plastic (such as an acrylic polymer like PMMA or a polystyrene polymer, in particular) containing the photoacid generator or a raw material liquid containing the photoacid generator dissolved in a solvent (such as 1,2-dichloroethane or methanol) to the upward-facing surface of the main body 11, namely the bottom of the well 10, by spin coating, casting, or other techniques and then curing the raw material liquid, the to-be-irradiated layer 12 capable of generating heat and acid upon irradiation with the laser light L can be formed. For example, by applying a polymer containing a thioxanthone-based sulfonic acid derivative having a thioxanthone backbone as the pigment structure and having a sulfonic acid as the acid precursor to the bottom of the well 10 of the main body 11 at a density of 200 µg/cm², the to-be-irradiated layer 12 having an average thickness of 2 µm can be formed on the bottom of the well 10. Alternatively, the main body 11 may be formed by using a material blend containing the photoacid generator, and the resulting main body has the function of the to-be-irradiated layer 12 capable of generating heat and acid upon irradiation with the laser light L.

The light absorbance by the to-be-irradiated layer 12 which has a certain thickness and is made by coating the main body 11 with a polymer that contains a thioxanthone-based sulfonic acid derivative having a thioxanthone backbone as the pigment structure and having a sulfonic acid as the acid precursor ranges from a light wavelength of about 375 nm to a light wavelength of about 460 nm. This means that a light having a wavelength outside this range is not absorbed by the to-be-irradiated layer 12 and the laser light L having a wavelength of 405 nm or 450 nm is absorbed by the to-be-irradiated layer 12. It should be noted that the light absorbance by this to-be-irradiated layer 12 is lower than the light absorbance by the to-be-irradiated layer 12 made by using a polymer that contains azobenzene as the pigment structure, and is lower than 20% (more specifically, even lower than 10%) at a visible-light wavelength ranging from about 400 nm to about 700 nm.

It is preferable that the material of the to-be-irradiated layer 12 generate no fluorescence upon irradiation with the laser light L. It is preferable that the thickness of the to-be-irradiated layer 12 be 10 µm or lower.

The surface of the to-be-irradiated layer 12 of the cell culture vessel 1 may be coated with an ingredient capable of enhancing cell adhesion, such as an ECM (extracellular matrix) like laminin or Matrigel.

For culturing cells, the well 10 formed in the main body 11 of the cell culture vessel 1 is filled with a culture medium (particularly, a liquid culture medium) 13. In other words, the culture medium 13 is positioned directly on the to-be-irradiated layer 12 disposed at the bottom of the well 10. The cells thus cultured adhere to and proliferate on the surface of the to-be-irradiated layer 12 and form cell aggregates 6.

As shown in FIG. 4, the laser processing for killing intended cells from among a group of cells in the well 10 in the cell culture vessel 1 is conducted in the following way. The laser light L discharged from the processing nozzle 33 of the laser irradiator 3 is directed to a partial area of the to-be-irradiated layer 12 of the cell culture vessel 1 supported on the support 2 directly below the cells to kill. In this embodiment with the processing nozzle 33 disposed below the cell culture vessel 1, the laser light L that has been discharged upward from the processing nozzle 33 passes through the main body 11 to reach the to-be-irradiated layer 12 from the back side of the to-be-irradiated layer. The built-in lens in the processing nozzle 33 focuses or directs the laser light L discharged from the processing nozzle 33 to the to-be-irradiated layer 12 of the cell culture vessel 1. The partial area of the to-be-irradiated layer 12 irradiated with the laser light L absorbs energy of the laser light L and thereby generates heat and/or acid. This heat kills unwanted cells that are present directly above the partial area.

In the case where the to-be-irradiated layer 12 comprises a photoacid generator, an acidic substance is generated in the partial area of the to-be-irradiated layer 12 irradiated with the laser light L and induces death of unwanted cells present directly above the partial area or induces detachment of these cells from the to-be-irradiated layer 12. In the case where the photoacid generator is a sulfonic acid derivative, the acidic substance thus generated is a sulfonic acid.

For example, the wavelength of the laser L is 405 nm, the output of the laser L is between 0.4 W and 5 W. Of course, the output may be over 5 W. Also, the diameter of the laser beam L is less than or equal to 50 µm. The rate of moving the processing nozzle 33 discharging the continuous-wave laser L or the high-frequency pulsed laser L which is almost like a continuous-wave laser, or the rate of moving the laser beam L, relative to the cell culture vessel 1 is set to between 50 mm/second and 2000 mm/second. When the output of the laser L is 5 W, the diameter of the laser beam L is 50 µm, and the rate of moving is 1500 mm/second, the partial area irradiated with the laser light L receives energy (energy density) of the laser light L of about 8.7 J/cm$^2$ per unit area. Even though the laser L with the above wavelength, output and energy amount cannot kill cells upon direct irradiation, the to-be-irradiated layer 12 acts to make it possible to adequately kill unwanted.

In order to minimize the influence of heat on cells other than cells to be killed, namely desired cells or tissues near unwanted cells, it is preferable that each of the wavelength, the output, and the energy amount of the laser light L to be applied to the to-be-irradiated layer 12 of the cell culture vessel 1 be adjusted to such a level that kills unwanted cells not instantly but after a certain period of time (for example, after several dozen minutes or after one to several hours, typically after 60 minutes or after 120 minutes) of irradiation with the laser light L. It is actually possible to create a state where unwanted cells are alive right after irradiation with the laser light L and then are killed after a certain period of time of the irradiation.

The width or size of the area occupied by dead cells can be increased or decreased by controlling the output or the per-unit-area energy amount of the laser L. As the output and/or the per-unit-area energy amount of the laser L increases, the width or size of the area occupied by dead cells increases.

In addition, it is expected that the time period after irradiation with the laser L until the death of unwanted cells decreases as the output and/or the per-unit-area energy amount of the laser L increases.

Suitable conditions for the output and/or the per-unit-area energy amount of the laser L used in laser processing are affected by the material, the thickness, and other characteristics of the to-be-irradiated layer 12 of the cell culture vessel 1. The amount of heat generation by a unit area of the to-be-irradiated layer 12 irradiated with the laser light L through absorption of energy of the laser light L is obtained by multiplying the amount of energy per unit area of the laser light L applied to the to-be-irradiated layer 12 by a factor of light utilization. The factor of light utilization refers to the rate at which a unit area of the to-be-irradiated layer 12 absorbs and utilizes energy of the laser light L. The factor of light utilization depends not only on the characteristics of (more specifically, the light absorbance by) the material of the to-be-irradiated layer 12 but also on the amount of a certain ingredient (per unit area of the to-be-irradiated layer 12) contributing to photo-thermal reaction in which heat is generated upon absorption of the laser light L. When the coating thickness of the material that forms the to-be-irradiated layer 12 of the main body 11 increases, the amount of the ingredient contributing to photo-thermal reaction increases accordingly, leading to an increase in the factor of light utilization of the to-be-irradiated layer 12 per unit area. Such an increase in the factor of light utilization leads to an increase in the amount of heat generation by a unit area of the to-be-irradiated layer 12, facilitating cell death. In view of the circumstances above, it is required that the factor of light utilization by the to-be-irradiated layer 12 of the cell culture vessel 1 be considered and the output and/or the per-unit-area energy amount of the laser L suitable for killing unwanted cells be experimentally determined.

The laser processing machine and the cell culture vessel 1 can be favorably used to divide the cultured cell aggregate 6 into plural parts. In examples shown in FIGS. 5 and 6, the laser beam L is moved in a way that a grid is drawn on the cell culture vessel 1 and thereby the cells on the to-be-irradiated layer 12 directly above the grid irradiated with the laser L are killed, to be followed by obtaining the cell clumps 61 consisting of cells other than the cells on the grid. In other words, the cell aggregate 6 cultured on the cell culture vessel 1 are cut along the grid. The grid irradiated with the laser L corresponds to the cutting lines 62 separating one clump 61 and another clump 61.

Figure 5:
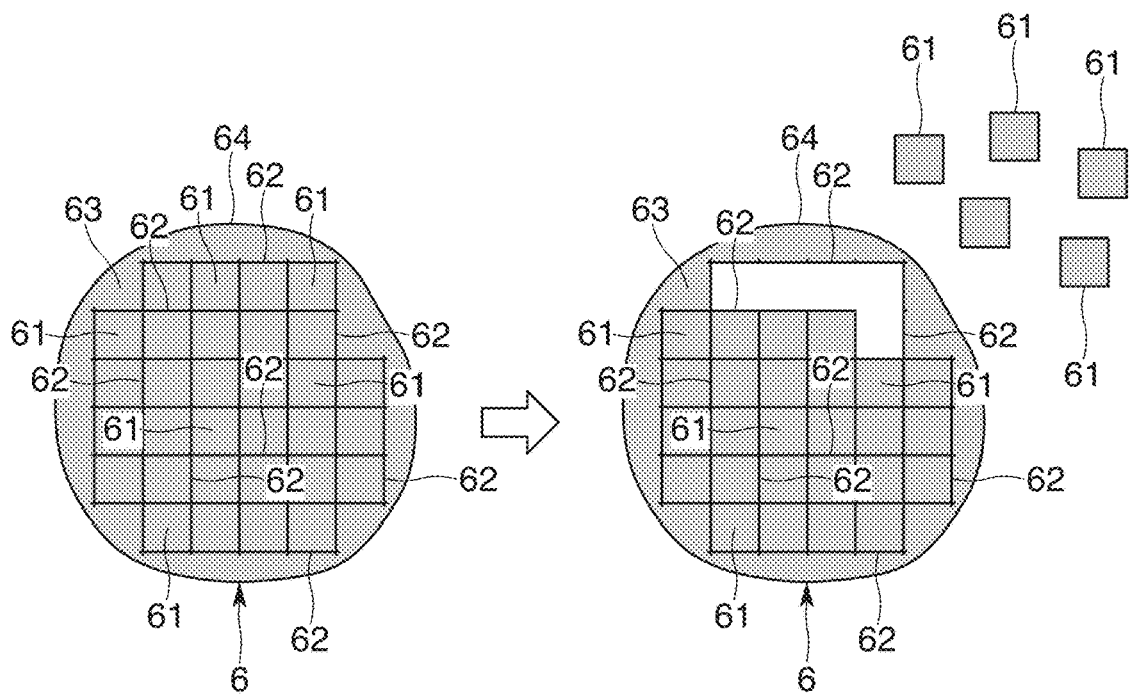
FIG. 5 is a plan view showing the progress of cutting out clumps with a cell processing method according to the embodiment.

In the example shown in FIG. 5, the laser beam L is linearly moved relative to the cell culture vessel 1 in the X-axis direction and the Y-axis direction, drawing many streaks in total parallel to each other at a certain intervals to form the grid. Both ends of the cutting lines 62 extended in the X-axis direction and the Y-axis direction do not reach the outer edge 64 of the cell aggregate 6. In order to move the laser beam L along such cutting lines 62, the control module 5, or the external device or computer coupled to the control module 5, detects the outer edge 64 of the cell aggregate 6 in the cell culture vessel 1, and sets the cutting lines 62 having lengths not to cross the outer edge 64, in other words, determines the plural X-Y coordinates on the cutting lines 62 as the coordinates of the target location which are irradiated with the laser light L. Then the control module 5 controls the position of the processing nozzle 33 and the timing of discharging the laser L from the processing nozzle 33 at the to-be-irradiated layer 12 of the cell culture vessel 1 so as to irradiate the plural X-Y coordinates on the cutting lines 62 with the laser L.

After the elapse of time for extinction of the cells on the cutting lines 62 from irradiation with the laser L, the clumps 61 consisting of the cells surrounded by the cutting lines 62 can be obtained. At this time, the clumps 61 detached from the cell culture vessel 1 may become rounded because those consist of living cells. If each of the clumps 61 which are cut out has adhesion as far as it can be easily detached from the surface of the to-be-irradiated layer 12 of the cell culture vessel 1, it is possible to float and retrieve the clumps 61 by adding culture solution or other liquid to the well 10 (or pour culture solution or other liquid over the clumps 61) without using an enzyme for detaching the cells. However, the enzyme is usable to detach the cells adhering to the cell culture vessel 1 from its surface.

When the cells on the cutting lines 62 are killed by irradiating with the laser L and the clumps 61 consisting of the cells surrounded by the cutting lines 62 are cut out, cells that are not cut out as the clumps 61 remain in a peripheral part 63 of the cell aggregate 6. The peripheral part 63 is not surrounded by the cutting lines 62, or the cutting lines 62 adjacent to the peripheral part 63 do not continuously come full circle around the peripheral part 63. The area of the peripheral part 63 which is not cut and is linked exceeds the area of one of the clumps 61. In particular, according to the examples shown in FIGS, controlling each of the cutting lines 62 so that both ends thereof do not reach the outer edge 64 of the cell aggregate 6 makes it possible to form the peripheral part 63 which continuously comes full circle and surrounds the plurality of the clumps 61. Since the area of the linked peripheral part 63 is larger than the area of one of the clumps 61, the adhesion of the cells which constitute the peripheral part 63 to the cell culture vessel 1 becomes stronger than the adhesion of the cells which constitute one of the clumps 61 to the cell culture vessel 1. Therefore the possibility that the cells constituting the peripheral part 63 other than the clumps 61 come off the cell culture vessel 1 and contaminate the clumps 61 when each of the clumps 61 is detached from the cell culture vessel 1 is decreased, separation of the clumps 61 and the cells other than the clumps 61 is facilitated.

Figure 6:
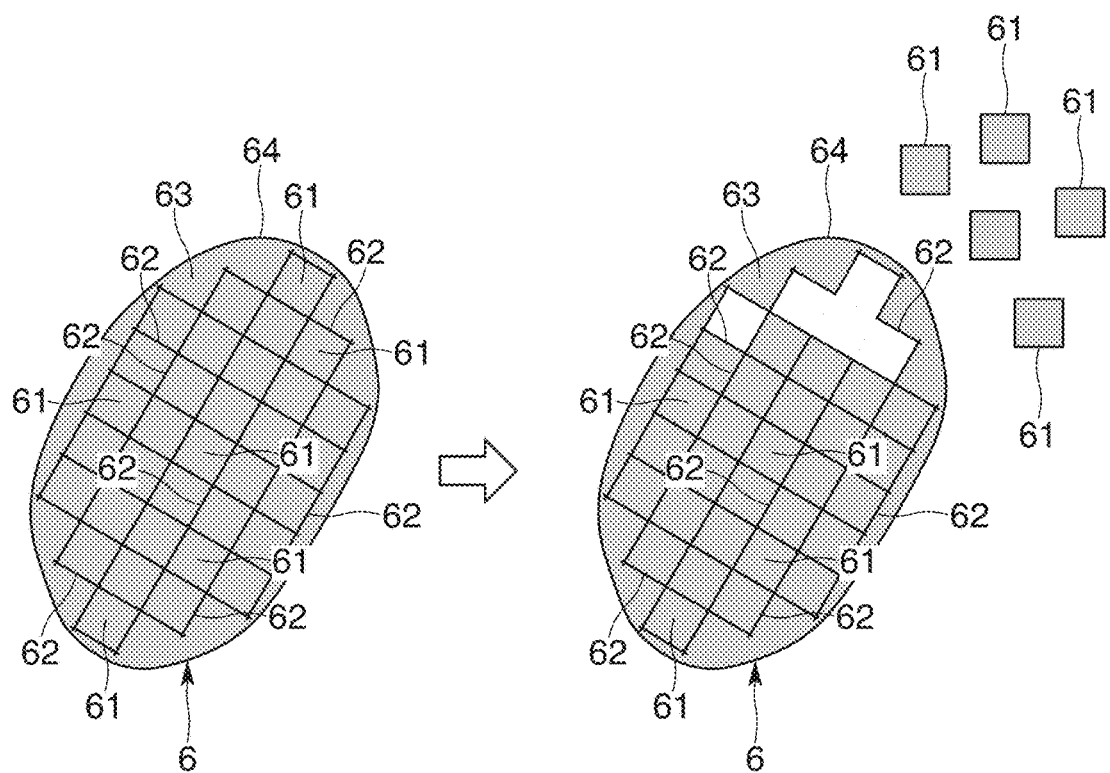
FIG. 6 is a plan view showing the progress of cutting out clumps with a cell processing method according to the embodiment.

In the example shown in FIG. 6, the laser beam L is linearly moved relative to the cell culture vessel 1 in the longitudinal direction of the cell aggregate 6 and the direction orthogonal to the longitudinal direction, drawing many streaks in total parallel to each other at a certain intervals to form the grid. Both ends of the cutting lines 62 extended in the longitudinal direction of the cell aggregate 6 and the direction orthogonal to the longitudinal direction do not reach the outer edge 64 of the cell aggregate 6. In order to move the laser beam L along such cutting lines 62, the control module 5, or the external device or computer coupled to the control module 5, detects the outer edge 64 of the cell aggregate 6 in the cell culture vessel 1, determines the longitudinal direction of the cell aggregate 6, and sets the cutting lines 62 having lengths not to cross the outer edge 64. Then the control module 5 controls the position of the processing nozzle 33 and the timing of discharging the laser L from the processing nozzle 33 so as to irradiate the plural X-Y coordinates on the cutting lines 62 with the laser L.

Figure 7:
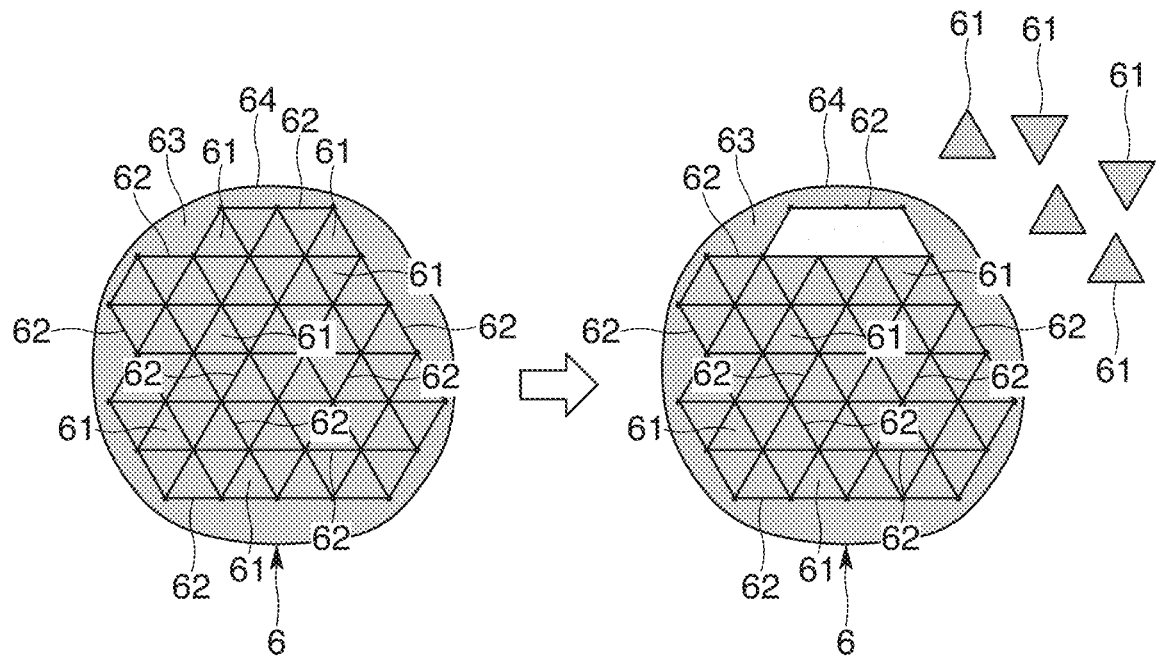
FIG. 7 is a plan view showing the progress of cutting out clumps with a cell processing method according to the embodiment.

In an example shown in FIG. 7, the laser beam L is moved in a way that a triangular lattice is drawn on the cell culture vessel 1 and thereby the cells on the to-be-irradiated layer 12 directly above the triangular lattice irradiated with the laser L are killed, to be followed by obtaining the cell clumps 61 consisting of cells other than the cells on the triangular lattice. In other words, the cell aggregate 6 cultured on the cell culture vessel 1 are cut along the triangular lattice.

In this situation, the control module 5, or the external device or computer coupled to the control module 5, detects the outer edge 64 of the cell aggregate 6 in the cell culture vessel 1, and sets the cutting lines 62 having lengths not to cross the outer edge 64 so that both ends of the cutting lines 62 do not reach the outer edge 64 of the cell aggregate 6. Then the control module 5 controls the position of the processing nozzle 33 and the timing of discharging the laser L from the processing nozzle 33 so as to irradiate the plural X-Y coordinates on the cutting lines 62 with the laser L.

Figure 8:
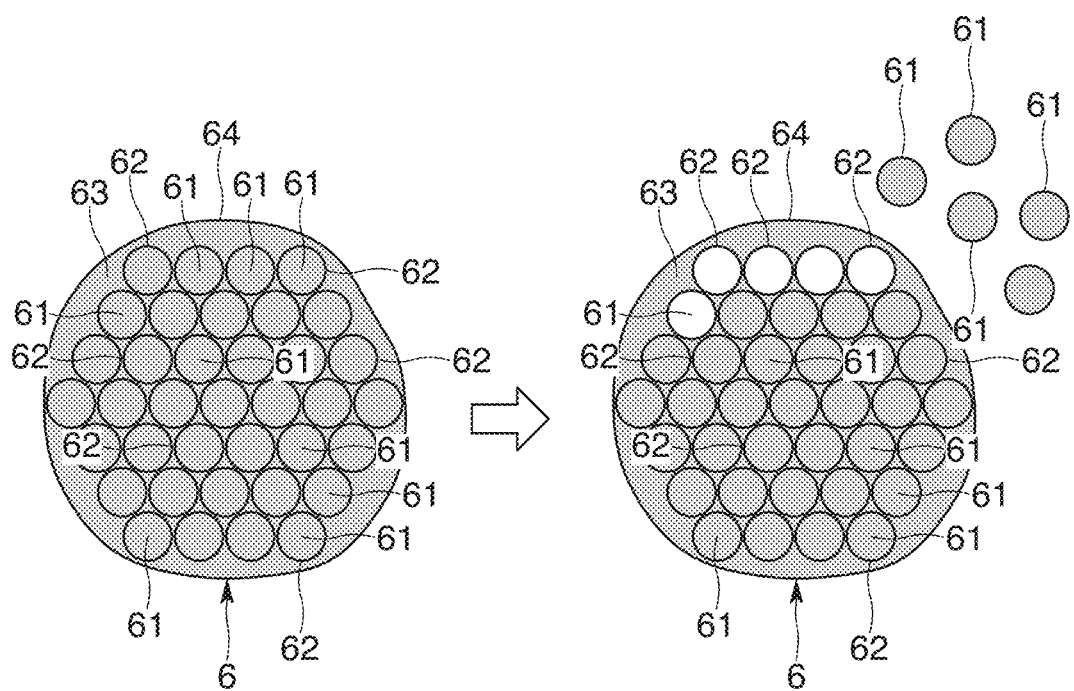
FIG. 8 is a plan view showing the progress of cutting out clumps with a cell processing method according to the embodiment.

In an example shown in FIG. 8, the laser beam L is moved in a way that many closed circles (more specifically, rounds) are drawn on the cell culture vessel 1 and thereby the cells on the to-be-irradiated layer 12 directly above the circles irradiated with the laser L are killed, to be followed by obtaining the cell clumps 61 consisting of cells in the circles. In other words, the cell aggregate 6 cultured on the cell culture vessel 1 are cut along the cutting lines 62 formed into the closed circles, just like die cutting. Even though the cutting lines 62 are perfect circles according to the example shown in FIG. 8, those may be formed into an elliptic shape, a hexagonal shape, or any other polygon.

In this situation, the control module 5, or the external device or computer coupled to the control module 5, detects the outer edge 64 of the cell aggregate 6 in the cell culture vessel 1, and sets the plural of the circular cutting lines 62 having lengths not to cross the outer edge 64 so that both ends of the circular cutting lines 62 do not reach the outer edge 64 of the cell aggregate 6. Then the control module 5 controls the position of the processing nozzle 33 and the timing of discharging the laser L from the processing nozzle 33 so as to irradiate the plural X-Y coordinates on the cutting lines 62 with the laser L.

The cell processing method according to this embodiment for cutting the plurality of the clumps 61 having approximately uniform dimensions out of the cell aggregate 6 which has proliferated is characterized by setting the cutting lines 62 along which the clumps 61 of a specific shape are cut out such that the area of the peripheral part 64 of the cell aggregate 6 which is not cut by the cutting lines 62 exceeds the area of one of the clumps 61. The laser processing machine according to this embodiment irradiates the cutting lines 62 set in that way with the laser light L tracing the cutting lines 62 so as to cut the cell aggregate 6.

The cell processing method above as well as use of the laser processing machine and the cell culture vessel 1 according to this embodiment can kill specific cells from among a group of cells cultured in the cell culture vessel 1 by quick and brief laser processing. Raster scanning with the laser beam L across a certain region of (the to-be-irradiated layer 12 of) the cell culture vessel 1 can kill not only the unwanted cells that have not differentiated into desired cells, among the cell aggregate 6 on the cell culture vessel 1, but also all the cells present within the region.

In particular, killing the cells which exist in the peripheral part 63 (and are not used as the clumps 61) by raster scanning with the laser beam L across the peripheral part 63 after or before applying the laser L to the cell aggregate 6 along the cutting lines 62 decreases the possibility that the cells constituting the peripheral part 63 come off together when the clumps 61 are detached from the cell culture vessel 1 (with using the enzyme, and so on). In other words, the clumps 61 are not contaminated with fragments of unwanted cells. It should be noted that one end or both ends of the cutting lines 62 may reach the outer edge 64 of the cell aggregate 6 in this situation.

By applying the laser L to the partial area of the to-be-irradiated layer 12 directly below the cutting lines 62 between any two portions of the group of cells cultured in the cell culture vessel 1, the group of cells can be divided into each portion. This technique is effective for easy collection of the cell clumps 61 having a uniform size, for subculturing.

The diameter of the laser beam L for irradiation of the cell culture vessel 1 can be as small as 50 μm or lower. So, a small cell of 20 μm or smaller, like a human iPS cell, can be adequately treated.

By irradiating the partial area of the to-be-irradiated layer 12 of the cell culture vessel 1 directly below the specific cells with the laser light L that has the right level of output or energy amount to kill the specific cells not instantly but after a certain period of time, the effect of heat on other cells near the specific cells can be minimized, leading to a further increase in the yield of desired cells or tissues.

The present invention is not limited to the above-described embodiment. The wavelength of the laser L for laser processing to kill unwanted cells is not limited to 405 nm. In the case where the laser L having a different wavelength is used, the to-be-irradiated layer 12 of the cell culture vessel 1 needs to be made by using an ingredient (particularly, a polymer) having a pigment structure capable of absorbing a light having that wavelength. In the case where a near-infrared laser L having a wavelength of 808 nm or 1064 nm is used, for example, a phthalocyanine (a phthalocyanine derivative or a near-infrared-absorbing phthalocyanine pigment) may be used. In this case, it is desirable that the phthalocyanine be immobilized on a side chain of the polymer via a chemical bond so that the phthalocyanine does not enter into cells. Use of a coordinated complex, even one capable of forming a polymer, should be avoided because such a complex may release a metal ion.

The diameter of the laser beam L may be smaller than 50 μm. By connecting an optical fiber having a small core diameter to the processing nozzle 33 and then making the laser light L emitted from the laser source 31 pass through the optical fiber to the processing nozzle 33, for example, the diameter of the laser beam L discharged from the processing nozzle 33 can be made to 25 μm or smaller and accordingly the amount of energy (energy density) of the laser L per unit area can be increased. In this case, even when the maximum output of the laser source 31 is not high, a considerable amount of energy can be applied to the area irradiated with the laser L, namely the partial area where unwanted cells are present.

The shape of projection of the laser beam L applied to the to-be-irradiated layer 12 is not limited to a spot or a circle. The shape of projection of the laser beam L may be a rod-like line beam extending toward a certain direction.

In the embodiment above, the laser beam L is moved relative to the cell culture vessel 1 to draw a grid so as to cut the cell clumps 61 for subculturing. The path of movement of the laser beam L is not limited to a grid-shape. For example, the laser beam L may be moved relative to the cell culture vessel 1 so as to draw a hexagon mesh (or a honeycomb arrangement) consisting of a plurality of regular hexagons right next to each other on the to-be-irradiated layer 12, more specifically, so as to kill cells along the hexagon mesh. In this case, living cells remaining inside each hexagon that constitutes the cutting lines 62 are used as the cell clump 61.

In the embodiment above, the processing nozzle 33 configured to discharge the laser L toward the cell culture vessel 1 supported on the support 2 is mounted on the XY stage 4 and the processing nozzle 33 is moved in the X-axis direction and in the Y-axis direction. An alternative configuration may also be adopted where the support 2 supporting the cell culture vessel 1 is mounted on the displacement mechanism 4 such as the XY stage and the cell culture vessel 1 is moved in the X-axis direction and in the Y-axis direction. A yet another alternative configuration may also be adopted where one of the processing nozzle 33 and the support 2 is mounted on a linear-motor sliding platform or the like that can move in the X-axis direction and the other of these is mounted on a linear-motor sliding platform or the like that can move in the Y-axis direction, thereby the laser beam L discharged from the processing nozzle 33 being displaced in both the X-axis direction and the Y-axis direction relative to the to-be-irradiated layer 12 of the cell culture vessel 1.

The displacement mechanism 4 for displacing the target location of the laser L on the to-be-irradiated layer 12 of the cell culture vessel 1 may be a galvano scanner. As is well known, a galvano scanner is configured to turn a mirror that reflects the laser light L emitted from the laser source 31 with the use of a servo motor or a stepping motor, for example, allowing the mirror to quickly change the optical axis of the laser L. It should be noted that, in the case where a galvano scanner is used, the angle at which the optical axis of the laser light L crosses with the to-be-irradiated layer 12 of the cell culture vessel 1 cannot be maintained precisely constant. In the case where a semiconductor laser or the like is used as the laser source and the laser oscillated by the laser source is transferred to the galvano scanner through an optical fiber or the like, it is not easy to minimize the diameter of the laser beam L to be applied to the to-be-irradiated layer 12 or to minimize the scale of projection of the laser beam. For minimizing the diameter of the laser beam L or the scale of projection of the laser beam so as to enhance energy density, it is preferable to use a mechanism, such as the XY stage 4 or a linear-motor sliding platform, capable of moving the optical axis of the laser beam L in a direction parallel to the to-be-irradiated layer 12 of the cell culture vessel 1. By using a fiber laser as the laser source or converging solid-state laser light, the diameter of the laser beam L to be applied to the to-be-irradiated layer 12 or the scale of projection of the laser can be minimized.

A camera sensor for taking an image of cells in the cell culture vessel 1 may be disposed on the processing nozzle 33.

As the light source for providing light for taking an image of cells in the cell culture vessel 1, the laser light L discharged from the processing nozzle 33 may be used. In this case, the output of the laser L discharged from the processing nozzle 33 for irradiating the cell culture vessel 1 needs to be adequately lower than the output of the laser L to be applied to the cell culture vessel 1 for killing unwanted cells.

In the embodiment above, the to-be-irradiated layer 12 is formed by coating the bottom of the well 10 in the main body 11 of the cell culture vessel 1 with a polymer that is a material of the to-be-irradiated layer 12. However, it is difficult to coat the entire multidish-shape main body having a plurality of wells formed thereon with the polymer by a technique such as spin coating so as to form the to-be-irradiated layer. In view of this circumstance, an alternative configuration may also be adopted where an ingredient capable of generating heat upon irradiation with the laser light L is used to make a plate and the resulting plate is disposed on or attached to the bottom of each well in the main body to form the to-be-irradiated layer of the cell culture vessel. The plate may be made by applying a pigment capable of absorbing the laser light L to a sheet of a material, such as plastic or glass, that is transparent or light-transmissive to allow the passage of the laser light L. Alternatively, the sheet may be made with a material blend containing a pigment capable of absorbing the laser light L. Yet alternatively, the pigment-structure-containing polymer or the photoacid generator in the embodiment above may be used as the pigment capable of absorbing the laser light L.

In the embodiment above, the to-be-irradiated layer 12 is irradiated with the laser light L that is emitted from below the cell culture vessel 1 and then passes through the main body 11. An alternative configuration may also be adopted where the to-be-irradiated layer 12 is directly irradiated with the laser light L emitted from above, namely from the side of the surface of the to-be-irradiated layer 12 (without the laser light passing through the main body 11). In this case, it is not necessary for the main body 11 to be transparent or light-transmissive for allowing the passage of the laser light L. It is preferable that the focus of the laser light L for irradiation be adjusted not on cells on the to-be-irradiated layer 12 but on the to-be-irradiated layer 12.

For culturing iPS cells and other cells in the cell culture vessel 1, feeder cells may be concurrently used. The laser processing machine according to the present invention can also be used to kill feeder cells no longer required in the cell culture vessel 1.

In the case where a plural of clumps 61 are cut out of a cell aggregate 6 which has proliferated in a cell culture vessel 1 without the to-be-irradiated layer 12 formed, it is possible to focus laser light L discharged from a processing nozzle 33 of the laser processing machine to a layer of the cell aggregate 6 on the cell culture vessel and directly irradiate the cell aggregate 6 with the laser light L so as to kill cells on cutting lines 62. In this case, the laser L may be a pulsed laser like a picosecond laser or a femtosecond laser with an ultrashort pulse width.

It is conceivable that the cutting of the cell aggregate 6 be carry out with a micro needle, a micro blade, or the like instead of the laser processing machine. That is, the micro needle or blade may be moved along the cutting lines 62 which are set to cut the clumps 61 out of the cell aggregate 6, and cut the cell aggregate 6 along the cutting lines 62, to be followed by obtaining the plural cell clumps 61 similarly to the above embodiment.

Regarding to the concrete configurations of the respective components, various modifications are possible without departing from the scope and spirit of the present invention.

INDUSTRIAL APPLICABILITY

The present invention is applicable to cutting a plurality of clumps having approximately uniform dimensions out of a cell aggregate which has cultured in a cell culture vessel.

DESCRIPTION OF THE REFERENCE SIGNS

1: Culture vessel
11: Main body
12: To-be-irradiated layer
3: Laser irradiator
33: Processing nozzle
4: Displacement mechanism (XY stage)
5: Control module
6: Cell aggregate
61: Clump
62: Cutting lines
63: Peripheral part
64: Outer edge
L: Laser light

The invention claimed is:

1. A cell processing method of a cell aggregate which has adhered to a cell culture vessel, the cell processing method comprising:
   setting cutting lines along which a plurality of clumps of a specific shape are to be formed such that an area of a peripheral part of the cell aggregate, which does not include the cutting lines, exceeds an area of an individual clump of the plurality of clumps, wherein the setting of the cutting lines comprises acquiring one or more X-Y coordinates based on an analyzed image of the cell aggregate and the peripheral part having an inner periphery defined by an outer periphery of the cutting lines and the peripheral part continuously surrounding the outer periphery of the cutting lines;
   cutting the cell aggregate adhering to the cell culture vessel along the cutting lines to form the plurality of clumps and to form the peripheral part based on the acquired one or more X-Y coordinates, wherein the peripheral part of the cell aggregate adhering to the cell culture vessel is not cut so as to continuously surround the plurality of clumps; and
   with the peripheral part adhered to the cell culture vessel, removing the plurality of clumps.

2. The cell processing method according to claim 1, wherein the cutting comprises irradiating the cell aggregate with laser light in such a way as to trace the cutting lines.

3. The cell processing method according to claim 1, wherein the cutting comprises cutting the cell aggregate along the cutting lines to form each of the plurality of clumps to have one of a closed circle shape or an elliptic shape.

4. The cell processing method according to claim 1, wherein the cutting comprises cutting the cell aggregate along the cutting lines to form each of the plurality of clumps to have a uniform polygon shape.

5. The cell processing method according to claim 1, further comprising killing the peripheral part of the cell aggregate by irradiating the peripheral part with laser light.

6. The cell processing method according to claim 5, wherein the cutting is subsequent to the killing.

7. The cell processing method according to claim 1, wherein the cell aggregate is proliferated in a state of being adhered to the cell culture vessel.

8. The cell processing method according to claim 1, wherein the cutting step comprises emitting a light to a layer of the cell culture vessel, wherein the layer absorbs the light and cuts the cell aggregate.

* * * * *